(12) United States Patent
Zhou et al.

(10) Patent No.: US 11,795,089 B2
(45) Date of Patent: Oct. 24, 2023

(54) RESOURCE TREATMENT SYSTEM FOR URINE AND FECES SEPARATION AND RECOVERY IN URINE DIVERSION DEHYDRATION TOILETS

(71) Applicant: Tongji University, Shanghai (CN)

(72) Inventors: Xuefei Zhou, Shanghai (CN); Yalei Zhang, Shanghai (CN); Wenjun Yin, Shanghai (CN); Zhenjiang Yu, Shanghai (CN); Jiabin Chen, Shanghai (CN); Wei Zhang, Shanghai (CN); Yue Xu, Shanghai (CN)

(73) Assignee: TONGJI UNIVERSITY, Shanghai (CN)

( * ) Notice: Subject to any disclaimer, the term of this patent is extended or adjusted under 35 U.S.C. 154(b) by 434 days.

(21) Appl. No.: 17/084,647

(22) Filed: Oct. 30, 2020

(65) Prior Publication Data

US 2021/0130212 A1 May 6, 2021

(30) Foreign Application Priority Data

Nov. 1, 2019 (CN) .......................... 201911058871.8

(51) Int. Cl.
*C02F 11/02* (2006.01)
*C12M 1/00* (2006.01)
(Continued)

(52) U.S. Cl.
CPC ............. *C02F 11/02* (2013.01); *C12M 21/00* (2013.01); *C12M 23/02* (2013.01); *C12M 33/14* (2013.01);
(Continued)

(58) Field of Classification Search
CPC .... C02F 11/02; C02F 2103/005; C02F 1/444; C02F 1/4672; C02F 3/322;
(Continued)

(56) References Cited

U.S. PATENT DOCUMENTS

2010/0051542 A1\* 3/2010 Elektorowicz .......... C02F 3/005
204/627

FOREIGN PATENT DOCUMENTS

| CN | 107381930 A | \* | 5/2017 | ................ C02F 9/00 |
| CN | 109626551 A | \* | 4/2019 | ................ C02F 3/00 |

(Continued)

OTHER PUBLICATIONS

Translation of Mirqueza_NPL_2016.pdf (Year: 2016).\*
(Continued)

*Primary Examiner* — Ekandra S. Miller-Cruz
(74) *Attorney, Agent, or Firm* — Bayramoglu Law Offices LLC

(57) ABSTRACT

A resource treatment system for urine and feces separation and recovery in urine diversion dehydration toilets, includes a urine-faeces division toilet, a urine and gray water treatment system, and a fermentation and biodegradation fecal system. The urine-faeces division toilet is configured to separate and recover urine and feces discharged by users. The urine and gray water treatment system includes an adjusting pool, a microalgae culture device and a metal-based electrogenerated dynamic membrane. The adjusting pool is configured to receive the urine in the urine-faeces division toilet and domestic sewage, and adjust a urine-to-domestic sewage ratio. The metal-based electrogenerated dynamic membrane includes a metal microfiltration membrane, a stainless-steel mesh and a power supply. The fermentation and biodegradation fecal system includes a collection and adjusting device, a fermentation bed and a biodegradation chamber.

8 Claims, 3 Drawing Sheets

(51) Int. Cl.
*C12M 1/26* (2006.01)
*C12M 1/12* (2006.01)
*E04H 1/12* (2006.01)
*C02F 103/00* (2006.01)

(52) U.S. Cl.
CPC .......... *C12M 37/02* (2013.01); *E04H 1/1216* (2013.01); *C02F 2103/005* (2013.01)

(58) Field of Classification Search
CPC .......... C02F 2103/002; C02F 2103/20; C12M 21/00; C12M 23/02; C12M 33/14; C12M 37/02; C12M 21/02; C12M 31/00; E04H 1/1216; Y02W 10/20
USPC ........................................................ 210/605
See application file for complete search history.

(56) References Cited

FOREIGN PATENT DOCUMENTS

| | | | | |
|---|---|---|---|---|
| KR | 101694173 B1 | * | 1/2017 | ............... B05B 1/00 |
| WO | WO-2014057889 A1 | * | 4/2014 | ............ C12M 29/04 |

OTHER PUBLICATIONS

Translation of AKASHI_AKIRA_WO2014057889A1_NPL.pdf (Year: 2014).*
Translation of WANG_ZHIWEI_CN109626551A_NPL.pdf (Year: 2019).*
Du_QingPing_CN107381930A_NPL.pdf (Year: 2017).*
Translation of Nam (KR-101694173-B1) (Year: 2017).*

* cited by examiner

RESOURCE TREATMENT SYSTEM FOR URINE AND FECES SEPARATION AND RECOVERY IN URINE DIVERSION DEHYDRATION TOILETS

CROSS REFERENCE TO THE RELATED APPLICATIONS

This application is based upon and claims priority to Chinese Patent Application No. 201911058871.8, filed on Nov. 1, 2019, the entire contents of which are incorporated herein by reference.

TECHNICAL FIELD

The present invention relates to the fields of public health facilities and environmental energy, and more particularly, to a novel effective odor plugging bowl and a nutrition maximum utilization system for the separate urine and faces as well as the other agricultural wastes and domestic garbage.

BACKGROUND

The difficulty of improving toilets, especially in rural areas, is mainly reflected in the difficulty of manure resource utilization, often due to the high dispersion of rural population density and low building volume ratio. Although many rural areas continues to use manure, because of its low fertilizer efficiency and the inconvenient process, many farmers are gradually moving towards the more efficient chemical fertilizers.

SUMMARY

The technical problem to be solved by the present invention is to provide a treatment system that can process and recover urine and feces separately in urine diversion dehydration toilets for resource utilization.

In order to solve the above technical problem, the technical solution of the present invention is as follows. A resource treatment system for urine and feces separation and recovery in urine diversion dehydration toilets includes a urine-faeces division toilet, a urine and gray water treatment system, and a fermentation and biodegradation fecal system.

The urine-faeces division toilet is configured to separate and recover urine and feces discharged by users.

The urine and gray water treatment system includes an adjusting pool, a microalgae culture device and a metal-based electrogenerated dynamic membrane. The adjusting pool is configured to receive urine in the urine-faeces division toilet and domestic sewage, and adjust a urine-to-domestic sewage ratio. The adjusting pool is connected to the microalgae culture device through a pipe. The microalgae culture device can well utilize the carbon, nitrogen and phosphorus elements, and an outlet pipe of the microalgae culture device is further connected to the metal-based electrogenerated dynamic membrane. The metal-based electrogenerated dynamic membrane includes a metal microfiltration membrane, a stainless-steel mesh and a power supply. An anode of the power supply is connected to the metal microfiltration membrane, and a cathode of the power supply is connected to the stainless-steel mesh. The metal microfiltration membrane is configured to collect microalgae.

The fermentation and biodegradation fecal includes a collection and adjusting device, a fermentation bed and a biodegradation chamber. The collection and adjusting device is configured to receive the feces separated from the urine-faeces division toilet, kitchen waste and livestock and poultry feces, and adjust proportions of the feces, the kitchen waste and the livestock and poultry feces. The collection and adjusting device is connected to the fermentation bed. The fermentation bed ferments the mixture and feeds fermented residue into the biodegradation chamber.

Further, the microalgae culture device includes a culture column, a microalgae liquid, an illumination device and an aeration device. A water inlet and a water outlet are arranged on the culture column, and the microalgae liquid is arranged in the culture column. The aeration device is configured to aerate the liquid, and the illumination device is arranged above the culture column to provide light.

Further, a pore size of the metal microfiltration membrane is 5 μm or 10 μm, and a membrane surface is modified by polydopamine in-situ self-polymerization.

Further, the biodegradation chamber is a multi-stage degradation chamber, a first stage is a fly maggot degradation chamber, a second stage is an earthworm degradation chamber, and a third stage is a black soldier fly degradation chamber.

Further, the urine-faeces division toilet includes a rear urinal. The rear urinal is divided into a rear urine urinal and a feces pool by a partition arranged in the rear urinal. A urine collection port is arranged at a bottom of the rear urine urinal and connected to a urine storage bucket by a pipe. A feces bin is arranged under the feces pool. The feces pool is a hollow structure. The urine-faeces division toilet further includes a cover plate and a feces plate of the feces pool. The cover plate is located above the feces pool, and the feces plate is located under the feces pool. Both the cover plate and the feces plate are configured to rotate around a rotating shaft, and are linked with each other. When the cover plate is opened, the feces plate located under the feces pool is configured to separate the feces pool from the feces bin. When the feces plate is opened, the cover plate located above the feces pool is configured to cover an opening of the feces pool.

Further, the feces plate is a bending structure, and includes a sloping plate. When the cover plate is opened, the sloping plate is located under the feces pool to receive the feces. When the cover plate is closed, the sloping plate is turned over, and a surface for receiving the feces faces towards the feces pool. The feces plate and the cover plate are connected to rotate around a same rotating shaft and are directly fixedly connected. A raised pedal is further arranged on the cover plate for opening the cover plate.

Further, the urine-faeces division toilet further includes a receiving cavity for receiving plant ash. A plant ash channel is obliquely arranged under a bottom plate of the rear urine urinal. One end of the plant ash channel leads to the receiving cavity, and the other end of the plant ash channel is movably in contact with the sloping plate of the feces plate. A blanking baffle for opening or closing the plant ash channel is arranged the other end of the plant ash channel.

Further, a pedal is arranged at one side of the rear urinal, and the pedal is connected to a vertical valve rod. The blanking baffle rotates around a rotating shaft. A transmission plate is arranged at an end of the blanking baffle, and the valve rod abuts against the transmission plate. The valve rod moves downward to drive the transmission plate to rotate, and the transmission plate: enables the blanking baffle flip up to open the plant ash channel. When the valve rod is not affected by an external force, the blanking baffle is adhered to a port of the plant ash channel under the action of gravity to close the plant ash channel.

Further, the urine-faeces division toilet further includes a front urine urinal and a partition wall. The front urine urinal and the rear urinal are separated by the partition wall. A urine collection port is arranged at a bottom of the front urine urinal and connected to the urine storage bucket by a pipe.

Further, the receiving cavity is arranged in the partition wall, and the rear urine urinal is located between the front urine urinal and the rear feces pool.

DETAILED DESCRIPTION OF THE EMBODIMENTS

The embodiments of the present invention is clearly and completely described below with reference to the drawings.

Figure 1:
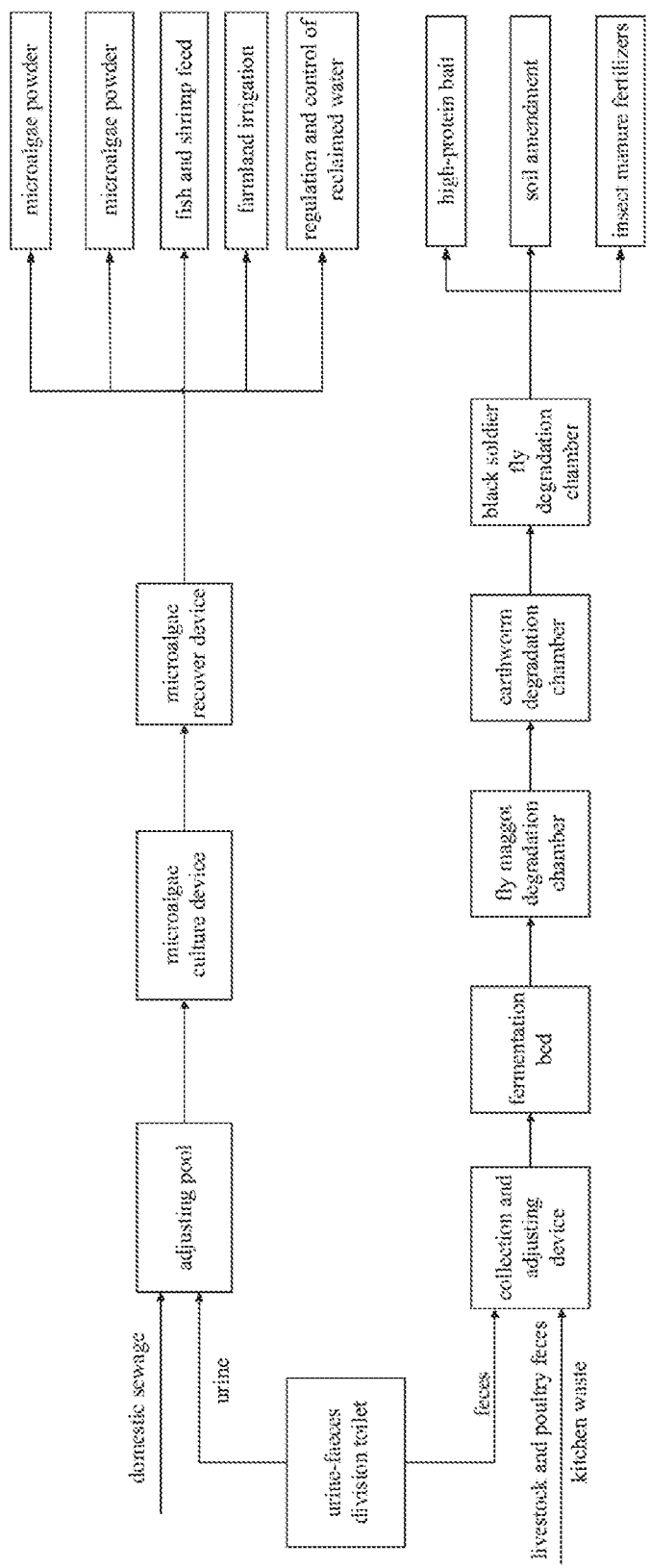
FIG. 1 is a flowchart of the present invention.

As shown in FIG. 1, a resource treatment system for urine and feces separation and recovery in urine diversion dehydration toilets of the present invention, includes a urine-faeces division toilet, a urine and gray water treatment system, and a fermentation and biodegradation fecal system.

Figure 2:
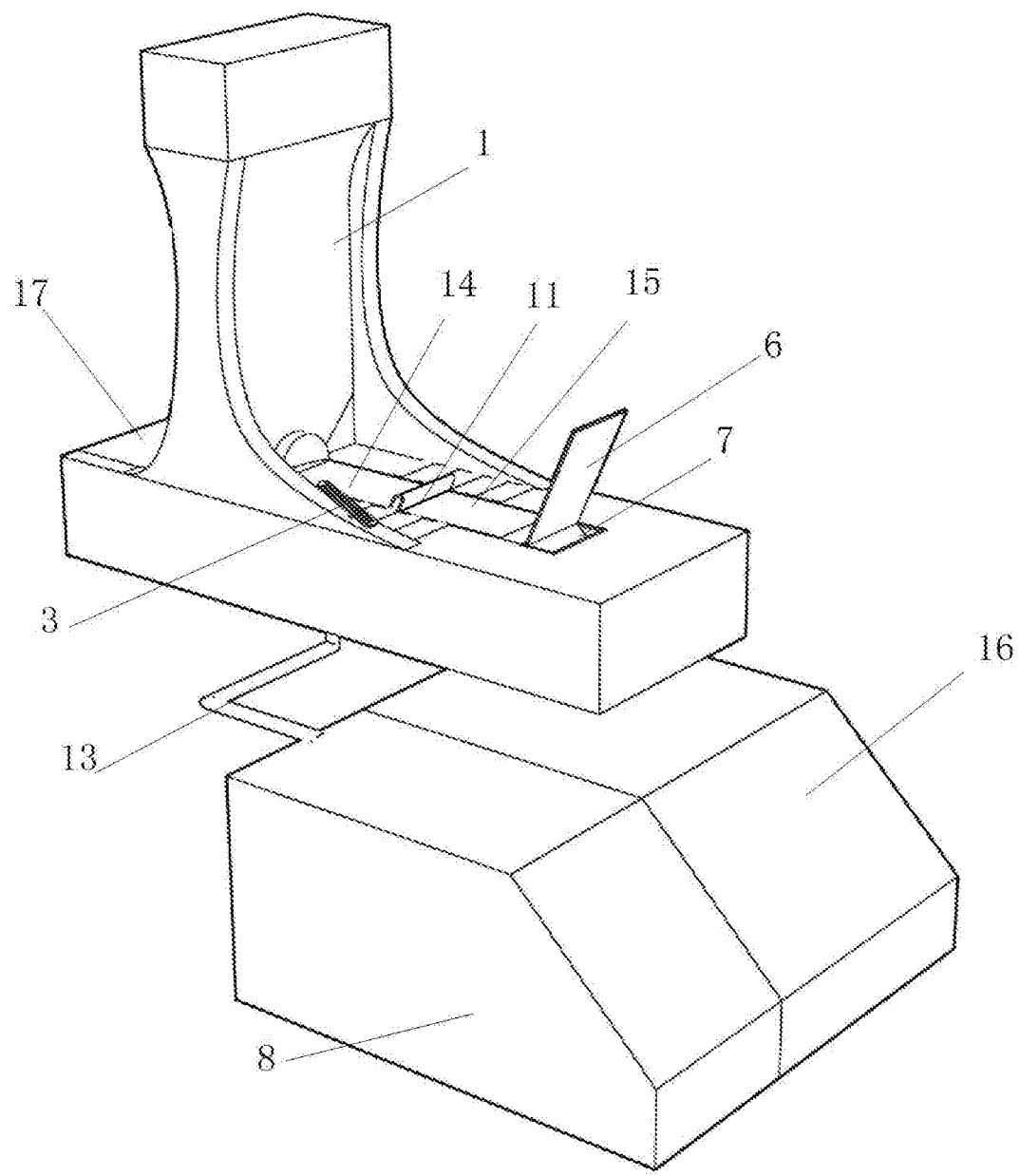
FIG. 2 is a schematic diagram of the structure of the urine-faeces division toilet according to the present invention.
Figure 3:
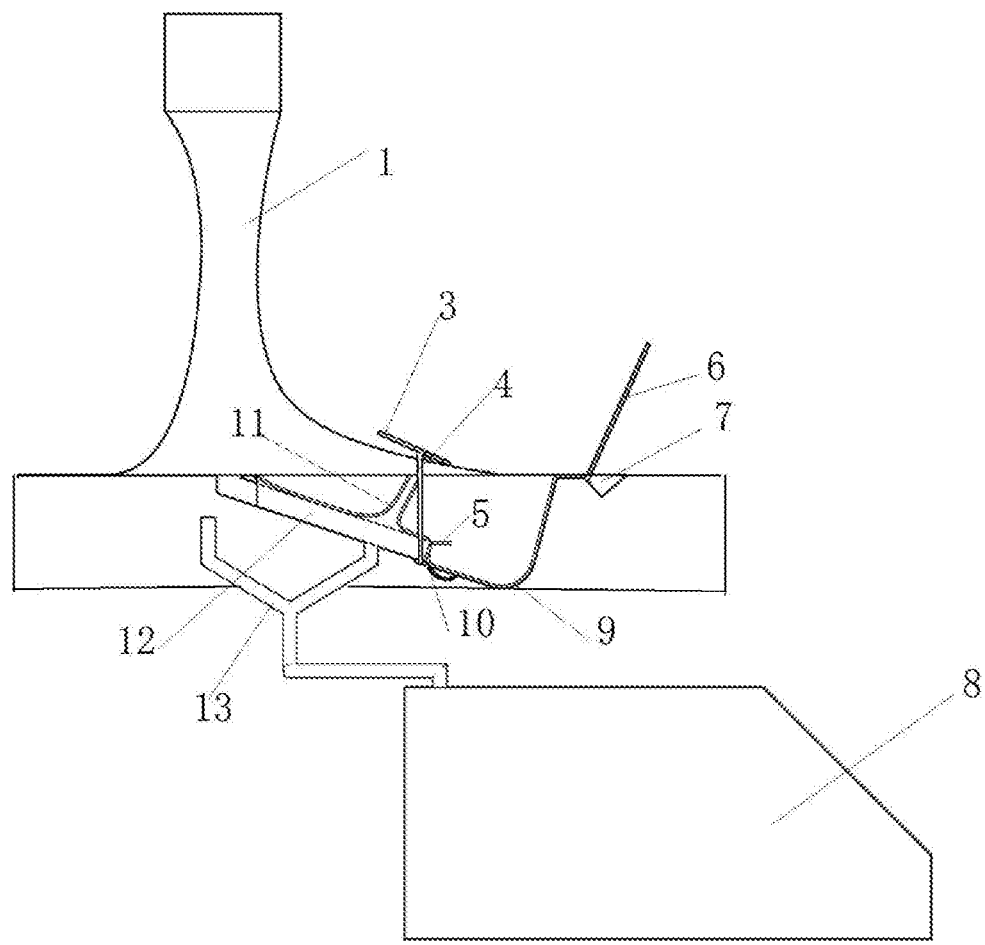
FIG. 3 is a schematic diagram of the inside structure of the urine-faeces division toilet according to the present invention.

The urine-faeces division toilet is configured to separate and recover urine and feces discharged by users, the specific structure of which is shown in FIGS. 2 and 3. The urine-faeces division toilet includes a rear urinal, which is divided into the rear urine urinal 14 and the feces pool 15 by the partition 11 arranged in the rear urinal. The partition 11 prevents urine in the urinal from entering the feces pool 15. A urine collection port is arranged at a bottom of the rear urine urinal and connected to the urine storage bucket 8 through the pipe 13. The feces bin 16 is arranged under the feces pool for storing feces. The feces pool 15 is a hollow structure.

The urine-faeces division toilet further includes the cover plate 6 and the feces plate 9 of the feces pool. The cover plate 6 is located above the feces pool 15, and the feces plate 9 is located under the feces pool. Both the cover plate 6 and the feces plate 9 are configured to rotate around a rotating shaft and are linked with each other. When the cover plate 6 is opened, the feces plate located under the feces pool is configured to separate the feces pool from the feces bin. When the feces plate is opened, the cover plate located above the feces pool is configured to cover an opening of the feces pool.

Specifically, the feces plate 9 is a bending structure that includes a sloping plate. When the cover plate is opened, the sloping plate is located under the feces pool to receive the feces. When the cover plate is closed, the sloping plate is turned over, and the surface for receiving the feces faces towards the feces pool. Moreover, the feces plate 9 can also be made into a spoon, which is more convenient for receiving feces. The feces plate and the cover plate are connected to rotate d a s rotating shaft and are directly fixedly connected. When the cover plate is rotated and closed, the feces plate can be automatically rotated to pour the received feces into the feces bin. In order to facilitate opening the cover plate, the raised pedal 7 is further arranged on the cover plate 6 for opening the cover plate.

Additionally, the urine-faeces division toilet includes a receiving cavity for receiving plant ash, and the plant ash channel 12 is obliquely arranged under a bottom plate of the rear urine urinal. One end of the plant ash channel 12 leads to the receiving cavity, and the other end of the plant ash channel 12 is movably in contact with the sloping plate of the feces plate 9. The blanking baffle 5 is arranged at the other end of the plant ash channel 12 for opening or closing the plant ash channel. The inclination angle of the plant ash channel is 50°-60°.

There are many ways to control the blanking baffle 5, for example, it can be controlled manually or by foot. The embodiment introduces a foot movement control method as follow. The pedal 3 is arranged at one side of the rear urinal, and the pedal 3 is connected to the vertical valve rod 4. The blanking baffle 5 rotates around a rotating shaft, and the transmission plate 10 is arranged at an end of the blanking baffle 5. The valve rod 4 abuts against the transmission plate 10. The valve rod moves downward to drive the transmission plate 10 to rotate, and the transmission plate 10 enables the blanking baffle to flip up to open the plant ash channel. When the valve rod is not affected by an external force, the blanking baffle 5 is adhered to a port of the plant ash channel under the action of gravity to close the plant ash channel.

In addition, the urine-faeces division toilet includes the front urine urinal 17 and the partition wall 1. The front urine urinal and the rear urinal are separated by the partition wall 1. A urine collection port is arranged at a bottom of the front urine urinal and connected to the urine storage bucket by a pipe. The receiving cavity is arranged in the partition wall, that is, the plant ash is stored in the partition wall, and the rear urine urinal is located between the front urine urinal and the rear feces pool.

The front urine urinal 17 is designed for male user during urination, and the rear urine urinal 14 is designed for female user. The urine from the two urine urinals flows into the closed urine storage bucket through a Y-shaped urine transmission pipe. During defecation when an user is sitting on the toilet, the user may step on the pedal 7 to open the cover plate, and the feces plate is synchronously converted from an unused state to a used state. When the user steps on the pedal 3, the blanking baffle is opened synchronously, and auxiliary materials such as plant ash and sawdust fall on the feces plate. The user's feces then fall into the feces bin and on the surface of the auxiliary material spread of the feces plate, and the smell of the feces is neutralized and absorbed to create a clean toilet environment; meanwhile, moisture in the feces is absorbed and reduced. After defecation is completed, the user may step on the pedal 3 again to open the blanking baffle again, and the auxiliary materials are spread on the surface of the feces, and the auxiliary materials cover and further mix the feces. At this time, the cover plate 6 is closed, the feces plate is turned over at the same time, and the fecal mixture mixed with auxiliary materials falls into the feces box.

The urine and gray water treatment system includes an adjusting pool, a microalgae culture device and a metal-based electrogenerated dynamic membrane. The adjusting pool is configured to receive the urine in the urine-faeces division toilet and domestic sewage, and adjust a urine-to-domestic sewage ratio. The adjusting pool is connected to the microalgae culture device through a pipe. The microalgae culture device absorbs carbon, nitrogen and phosphorus elements, and an outlet pipe of the microalgae culture device is further connected to the metal-based electrogenerated dynamic membrane. The metal-based electrogenerated dynamic membrane includes a metal microfiltration membrane, a stainless-steel mesh and a power supply. The anode of the power supply is connected to the metal microfiltration membrane, and the cathode of the power supply is connected to the stainless-steel mesh. The metal microfiltration membrane is configured to collect microalgae.

The microalgae culture device includes a culture column, a microalgae liquid, an illumination device and an aeration device. The culture column can be made of acrylic material, has a diameter of 15-20 cm, and is provided with a water inlet and a water outlet. Further, 20-30 culture columns are provided, and an aeration device is arranged in the culture column. The microalgae liquid is arranged in the culture column. The illumination device is arranged above the culture column.

A pore size of the metal microfiltration membrane is 5 μm or 10 μm. In order to achieve better contact between the membrane surface and the microalgae, a membrane surface of the metal-based microfiltration membrane is modified by polydopamine self-polymerization. The modification process is simple. The metal-based membrane is directly immersed in a 2 mg/mL dopamine solution with 50 mmol tris-HCl buffer solution (pH=8.5), and the self-polymerization time is generally 1-6 h, then microfiltration membranes with different hydrophilic surfaces can be obtained. The surface of the microalgae is usually negatively charged and easy to be captured by the positively charged interface. The modified metal microfiltration membrane is used as the anode, and the stainless-steel mesh is used as the cathode. The distance between the cathode and the anode is controlled at 3 cm, and the applied voltage is 1 V or 3 V, the specific choice of which depends on the concentration of the microalgae captured. The voltage can be used to control the actual pore size during the filtration of the membrane. The suction pump connected to the metal membrane is turned on, the microalgae forms a precoating layer on the membrane surface under the action of electrical attraction and suction force. The precoating layer will play an important role in the subsequent filtration process, which is very important to alleviate membrane pollution. Once the precoating layer is formed, the voltage can be adjusted to 0 V. After filtering for a period of time, the membrane filtration flux is reduced to 80% of the initial flux. At this time, the filter cake layer needs to be updated, which employs two main methods: the first way is to adopt air backwashing, wherein a proper amount of air is directly injected into the pump in reverse to realize the rapid removal and updating of the filter cake layer on the membrane surface; the second way is to rapidly oxidize and remove the microalgae layer on the surface by using ROS and ·OH generated by electrode oxidation through increasing the voltage to 10 V, so as to realize the rapid self-cleaning of the membrane surface.

The metal-based electrogenerated dynamic membrane can be used to recover the microalgae, and then the microalgae are dried into powder or stored as a high-concentration microalgae solution. The rich protein of the microalgae itself can be used as feed for fish and shrimp farming, which can extremely improve the meat quality of fish and shrimp, reduce the probability of fish and shrimp disease, and increase farmers' income by 10-30%. Moreover, the membrane filtration process can not only intercept the microalgae, but also achieve a bacterial interception percentage of approximately 100%, and the effluent can reach the standards of farmland irrigation or river and lake replenishment, which further realizes the efficient recycling of water resources.

The fermentation and biodegradation fecal system includes a collection and adjusting device, a fermentation bed and a biodegradation chamber. Specifically, the collection and adjusting device is configured to receive the feces separated from the urine-faeces division toilet, kitchen waste and livestock and poultry feces, and adjust proportions of the feces, the kitchen waste and the livestock and poultry feces. The kitchen waste is mainly food residue and oil-water. The collection and adjusting device is connected to the fermentation bed, and the fermentation bed ferments the mixture and feeds fermented residue into the biodegradation chamber. The biodegradation chamber is a multi-stage degradation chamber, in which a first stage is a fly maggot degradation chamber, a second stage is an earthworm degradation chamber, and a third stage is a black soldier fly degradation chamber. Fly maggot, earthworm and black soldier fly all decompose the feces from toilet and the organisms in kitchen waste for growth and reproduction, because they are natural protein bodies, they can be used in aquaculture, livestock and poultry breeding and others. The waste residue can be used, for example, to prepare ecological organic waste, soil amendments, insect manure fertilizers and others for agricultural production.

The present invention is based on the rural source separation toilet system. While realizing innovation for rural toilet technology, it can form a perfect ecological agriculture industrialization chain and create: considerable economic benefits by combining with microalgae cultivation, production of relevant high value-added products, crop planting, livestock and poultry breeding, and aquaculture. Through ecological chain construction based closed-circuit circulation, water-saving and water resources reuse, toilet excreta treatment and recycling and other key technologies research, the present invention minimizes the generation of rural sewage, avoids the random discharge of manure, reduces the environmental risk of pollutants, effectively solves the environmental pollution problem of rural toilets. Moreover, through the waste fertilizer preparation and resource utilization, the present invention promotes the green integration of toilet ecological chain and agricultural industry chain, realizes the ecological value-added of toilet system, and has significant environmental benefits.

What is claimed is:

1. A resource treatment system for urine and feces separation and recovery in urine diversion dehydration toilets, comprising
   a urine-faeces division toilet,
   a urine and gray water treatment system,
   a fermentation and biodegradation fecal system;
   wherein
   the urine-faeces division toilet is configured to separate and recover urine and feces discharged by users;
   the fermentation and biodegradation fecal system is configured to receive the feces separated from the urine-faeces division toilet;
   the urine and gray water treatment system comprises an adjusting pool, a microalgae culture device and a metal-based electrogenerated dynamic membrane; wherein
   the adjusting pool is configured to receive the urine in the urine-faeces division toilet and domestic sewage, and adjust a urine-to-domestic sewage ratio; the adjusting pool is connected to the microalgae culture device through a first pipe;
   the microalgae culture device comprises an outlet pipe, and the microalgae culture device is configured to absorb carbon, nitrogen and phosphorus elements; the outlet pipe of the microalgae culture device is connected to the metal-based electrogenerated dynamic membrane; and the metal-based electrogenerated dynamic membrane comprises a metal microfiltration membrane, a stainless-steel mesh and a power supply; an anode of the power supply is connected to the metal microfiltration membrane, and a cathode of the power supply is connected to the stainless-steel mesh; the metal microfiltration membrane is configured to collect microalgae, wherein a pore size of the metal microfiltration membrane is 5 μm or 10 μm, and a membrane surface of the metal microfiltration membrane is modified by polydopamine in-situ self-polymerization;

wherein the urine-faeces division toilet includes a rear urinal, wherein the rear urinal is divided into a rear urine urinal and a feces pool by a partition arranged in the rear urinal; a first urine collection port is arranged at a bottom of the rear urine urinal, and the first urine collection port is connected to a urine storage bucket by a second pipe; a feces bin is arranged under the feces pool; the feces pool is a hollow structure; and a cover plate is located above the feces pool, and a feces plate is located under the feces pool; the cover plate and the feces plate are configured to rotate around a first rotating shaft, and the cover plate and the feces plate are linked with each other; wherein when the cover plate is opened, the feces plate located under the feces pool is configured to separate the feces pool from the feces bin;

when the feces plate is opened, the cover plate located above the feces pool is configured to cover an opening of the feces pool.

2. The resource treatment system according to claim 1, wherein the microalgae culture device comprises a culture column, a microalgae liquid, an illumination device and an aeration device; a water inlet and a water outlet are arranged on the culture column, and the microalgae liquid is arranged in the culture column; the aeration device is configured to aerate the microalgae liquid, and the illumination device is arranged above the culture column to provide light.

3. The resource treatment system according to claim 1, wherein the feces plate is a bending structure, and the feces plate comprises a sloping plate; wherein when the cover plate is opened, the sloping plate is located under the feces pool to receive the feces;

when the cover plate is closed, the sloping plate is turned over, and a surface for receiving the feces faces towards the feces pool;

the feces plate and the cover plate are directly fixedly connected to rotate around the first rotating shaft; and a raised pedal is arranged on the cover plate for opening the cover plate.

4. The resource treatment system according to claim 3, wherein the urine-faeces division toilet further comprises a receiving cavity for receiving plant ash, and a plant ash channel is obliquely arranged under a bottom plate of the rear urine urinal; a first end of the plant ash channel leads to the receiving cavity, and a second end of the plant ash channel is movably in contact with the sloping plate of the feces plate; a blanking baffle for opening or closing the plant ash channel is arranged the second end of the plant ash channel.

5. The resource treatment system according to claim 4, wherein a pedal is arranged at a side of the rear urinal, and the pedal is connected to a vertical valve rod; the blanking baffle rotates around a second rotating shaft; a transmission plate is arranged at an end of the blanking baffle, and the vertical valve rod abuts against the transmission plate; the vertical valve rod moves downward to drive the transmission plate to rotate, and the transmission plate enables the blanking baffle to flip up to open the plant ash channel; when the vertical valve rod is not affected by an external force, the blanking baffle is adhered to a port of the plant ash channel under an action of gravity to close the plant ash channel.

6. The resource treatment system according to claim 5, wherein the urine-faeces division toilet further comprises a front urine urinal and a partition wall; the front urine urinal and the rear urinal are separated by the partition wall; a second urine collection port is arranged at a bottom of the front urine urinal, and the second urine collection port is connected to the urine storage bucket by a third pipe.

7. The resource treatment system according to claim 6, wherein the receiving cavity is arranged in the partition wall, and the rear urine urinal is located between the front urine urinal and the feces pool.

8. A resource treatment system for urine and feces separation and recovery in urine diversion dehydration toilets, comprising a urine-faeces division toilet, a urine and gray water treatment system, a fermentation and biodegradation fecal system;

wherein the urine-faeces division toilet is configured to separate and recover urine and feces discharged by users;

the urine and gray water treatment system comprises an adjusting pool, a microalgae culture device and a metal-based electrogenerated dynamic membrane; wherein the adjusting pool is configured to receive the urine in the urine-faeces division toilet and domestic sewage, and adjust a urine-to-domestic sewage ratio; the adjusting pool is connected to the microalgae culture device through a first pipe;

the microalgae culture device comprises an outlet pipe, and the microalgae culture device is configured to absorb carbon, nitrogen and phosphorus elements; the outlet pipe of the microalgae culture device is connected to the metal-based electrogenerated dynamic membrane; and the metal-based electrogenerated dynamic membrane comprises a metal microfiltration membrane, a stainless-steel mesh and a power supply; an anode of the power supply is connected to the metal microfiltration membrane, and a cathode of the power supply is connected to the stainless-steel mesh; the metal microfiltration membrane is configured to collect microalgae, wherein, the fermentation and biodegradation fecal system comprises a collection and adjusting device, a fermentation bed and a biodegradation chamber; wherein the collection and adjusting device is configured to receive the feces separated from the urine-faeces division toilet, kitchen waste and livestock and poultry feces, and adjust proportions of the feces, the kitchen waste and the livestock and the poultry feces to form a mixture;

the collection and adjusting device is connected to the fermentation bed; and the fermentation bed ferments the mixture and feeds fermented residue into the biodegradation chamber.

* * * * *